(12) United States Patent
Kusumi et al.

(10) Patent No.: US 11,805,860 B2
(45) Date of Patent: Nov. 7, 2023

(54) PREDICTION DEVICE, PREDICTION METHOD, AND PREDICTION SYSTEM

(71) Applicant: ASICS CORPORATION, Kobe (JP)

(72) Inventors: Hiroyuki Kusumi, Kobe (JP); Toshiaki Okamoto, Kobe (JP); Genki Hatano, Kobe (JP); Masaru Ichikawa, Kobe (JP)

(73) Assignee: ASICS CORPORATION, Kobe (JP)

( * ) Notice: Subject to any disclaimer, the term of this patent is extended or adjusted under 35 U.S.C. 154(b) by 0 days.

(21) Appl. No.: 18/064,029

(22) Filed: Dec. 9, 2022

(65) Prior Publication Data
US 2023/0200496 A1 Jun. 29, 2023

(30) Foreign Application Priority Data
Dec. 23, 2021 (JP) ................................. 2021-209086

(51) Int. Cl.
A43D 1/02 (2006.01)
(52) U.S. Cl.
CPC ...................... A43D 1/02 (2013.01)
(58) Field of Classification Search
CPC ....................................... A43D 1/02
USPC ....................................... 702/155
See application file for complete search history.

(56) References Cited

U.S. PATENT DOCUMENTS

| 2007/0142955 A1* | 6/2007 | Lin | A43D 1/025 12/146 L |
| 2008/0097720 A1* | 4/2008 | Tadin | A61B 5/1036 702/167 |
| 2016/0345664 A1* | 12/2016 | Kohatsu | A43B 13/186 |

FOREIGN PATENT DOCUMENTS

JP 5717894 B2 5/2015

* cited by examiner

Primary Examiner — Aditya S Bhat
(74) Attorney, Agent, or Firm — Studebaker & Brackett PC

(57) ABSTRACT

A prediction device includes: a communication device that acquires measurement subject data including measurement data of a shape of a foot of a measurement subject person in a loaded state; a storage that stores first sample data in the loaded state and second sample data in an unloaded state, the first sample data and the second sample data being calculated from measurement data of foot shapes of a plurality of samples, the samples being identical both in the loaded state and the unloaded state; and a processor that predicts the shape of the foot of the measurement subject person in the unloaded state. The processor calculates a difference between the measurement subject data and the first sample data, and predicts the shape of the foot of the measurement subject person in the unloaded state based on the difference and the second sample data.

9 Claims, 29 Drawing Sheets

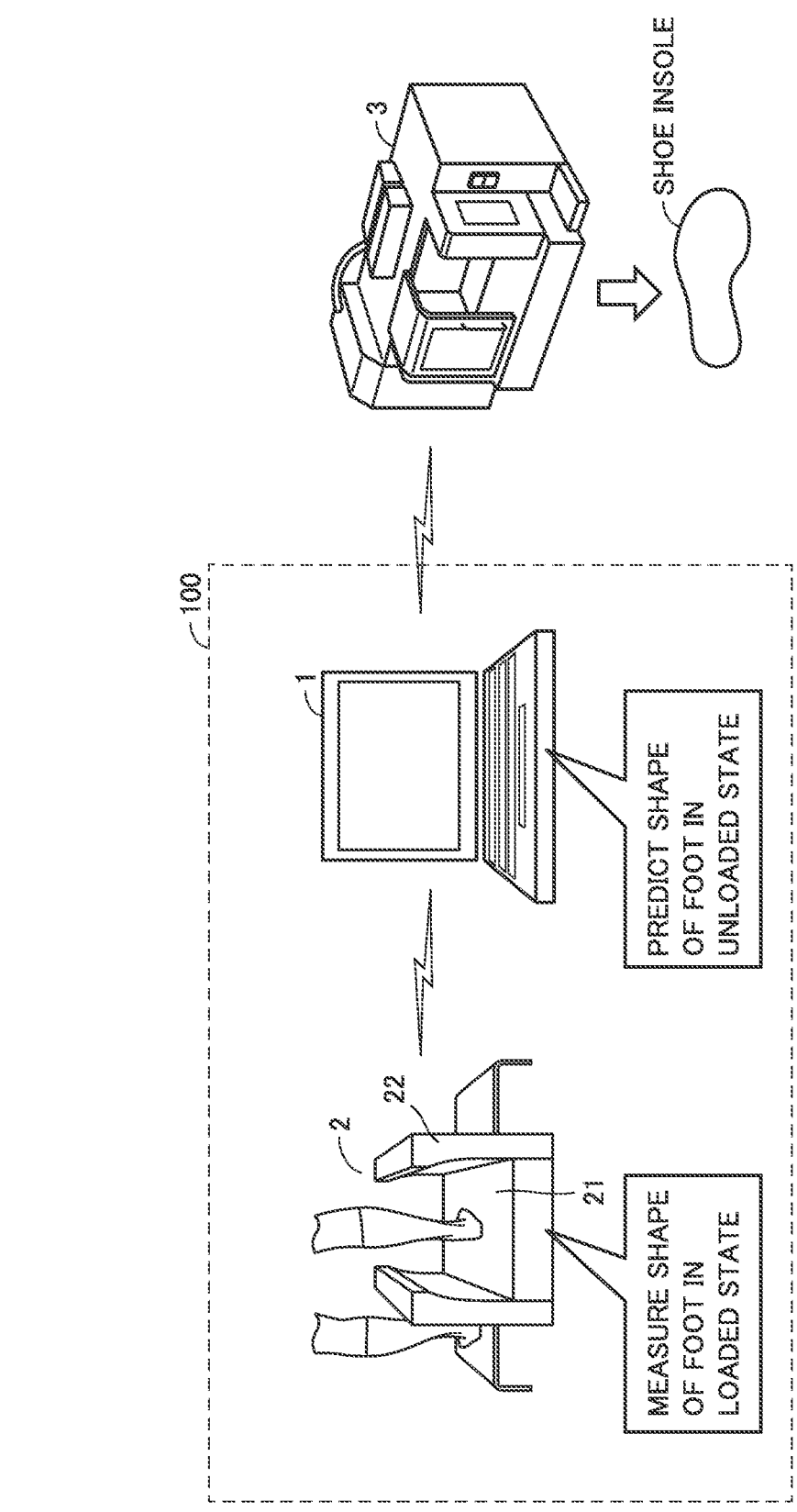

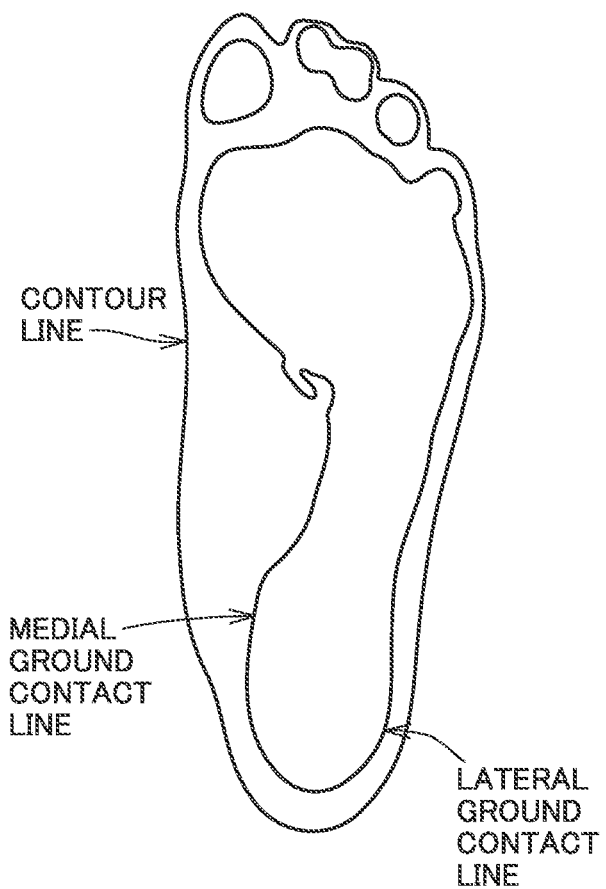

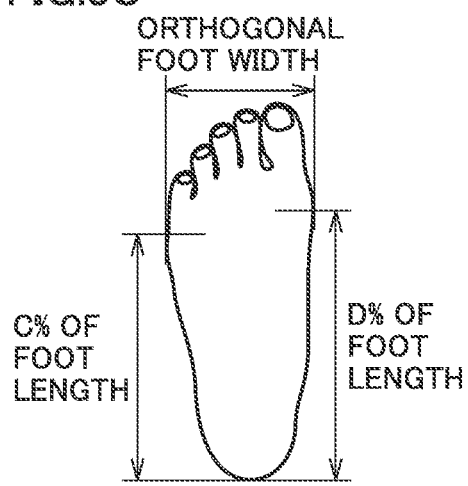

FIG.9

| LOADED FOOT SHAPE DATA (FIRST SAMPLE DATA) | | HEEL ANGLE | | |
|---|---|---|---|---|
| | | VALGUS | AVERAGE | VARUS |
| FOOT ARCH HEIGHT RATIO | HIGH ARCH | DATA A1 | DATA A2 | DATA A3 |
| | AVERAGE | DATA A4 | DATA A5 | DATA A6 |
| | FLAT | DATA A7 | DATA A8 | DATA A9 |

FIG.10

(A) MEASUREMENT

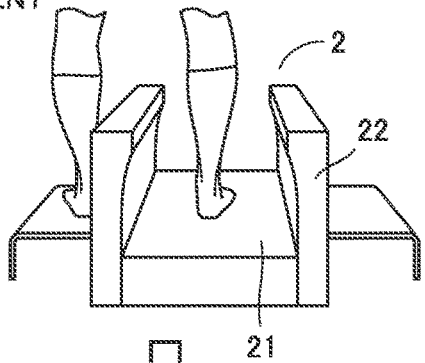

(B) CLASSIFICATION

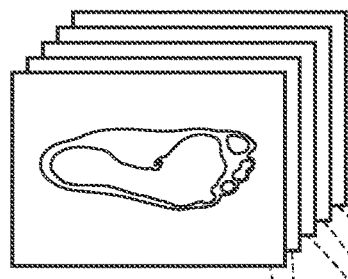

| LOADED FOOT SHAPE DATA (FIRST SAMPLE DATA) | | HEEL ANGLE | | |
|---|---|---|---|---|
| | | VALGUS | AVERAGE | VARUS |
| FOOT ARCH HEIGHT RATIO | HIGH ARCH | | | |
| | AVERAGE | | | |
| | FLAT | | | |

CONVERT FOOT LENGTH AND ORTHOGONAL FOOT WIDTH INTO REFERENCE FOOT LENGTH AND ORTHOGONAL FOOT WIDTH AND AVERAGE THEM (C) AVERAGING

| LOADED FOOT SHAPE DATA (FIRST SAMPLE DATA) | | HEEL ANGLE | | |
|---|---|---|---|---|
| | | VALGUS | AVERAGE | VARUS |
| FOOT ARCH HEIGHT RATIO | HIGH ARCH | DATA A1 | DATA A2 | DATA A3 |
| | AVERAGE | DATA A4 | DATA A5 | DATA A6 |
| | FLAT | DATA A7 | DATA A8 | DATA A9 |

FIG.11A

| CLASSIFICATION | | HEEL ANGLE | | |
| --- | --- | --- | --- | --- |
| | | VALGUS | AVERAGE | VARUS |
| FOOT ARCH HEIGHT RATIO | HIGH ARCH | TYPE 1 | TYPE 2 | TYPE 3 |
| | AVERAGE | TYPE 4 | TYPE 5 | TYPE 6 |
| | FLAT | TYPE 7 | TYPE 8 | TYPE 9 |

FIG.11B

| CLASSIFICATION | ORTHOGONAL FOOT WIDTH CONVERTED INTO REFERENCE FOOT LENGTH X mm |
|---|---|
| TYPE 1 | $Y_1$mm |
| TYPE 2 | $Y_2$mm |
| TYPE 3 | $Y_3$mm |
| TYPE 4 | $Y_4$mm |
| TYPE 5 | $Y_5$mm |
| TYPE 6 | Y6mm |
| TYPE 7 | Y7mm |
| TYPE 8 | Y8mm |
| TYPE 9 | Y9mm |

FIG.12

| UNLOADED FOOT SHAPE DATA (SECOND SAMPLE DATA) | | HEEL ANGLE | | |
|---|---|---|---|---|
| | | VALGUS | AVERAGE | VARUS |
| FOOT ARCH HEIGHT RATIO | HIGH ARCH | DATA B1 | DATA B2 | DATA B3 |
| | AVERAGE | DATA B4 | DATA B5 | DATA B6 |
| | FLAT | DATA B7 | DATA B8 | DATA B9 |

FIG.13

(A) MEASUREMENT

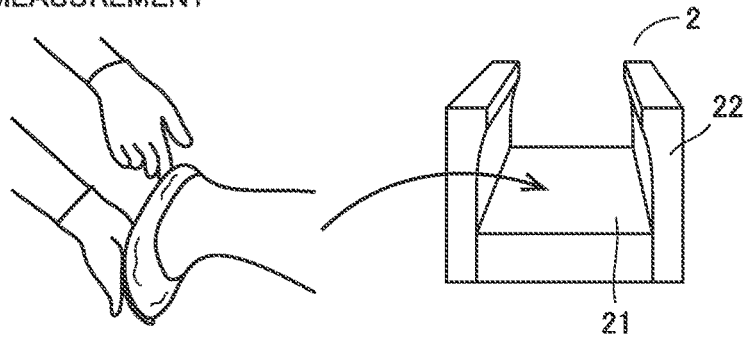

(B) CLASSIFICATION

| UNLOADED FOOT SHAPE DATA (SECOND SAMPLE DATA) | HEEL ANGLE | | |
|---|---|---|---|
| | VALGUS | AVERAGE | VARUS |
| FOOT ARCH HEIGHT RATIO — HIGH ARCH | | | |
| AVERAGE | | | |
| FLAT | | | |

CONVERT FOOT LENGTH AND ORTHOGONAL FOOT WIDTH INTO REFERENCE FOOT LENGTH AND ORTHOGONAL FOOT WIDTH AND AVERAGE THEM (C) AVERAGING

| UNLOADED FOOT SHAPE DATA (SECOND SAMPLE DATA) | HEEL ANGLE | | |
|---|---|---|---|
| | VALGUS | AVERAGE | VARUS |
| FOOT ARCH HEIGHT RATIO — HIGH ARCH | DATA B1 | DATA B2 | DATA B3 |
| AVERAGE | DATA B4 | DATA B5 | DATA B6 |
| FLAT | DATA B7 | DATA B8 | DATA B9 |

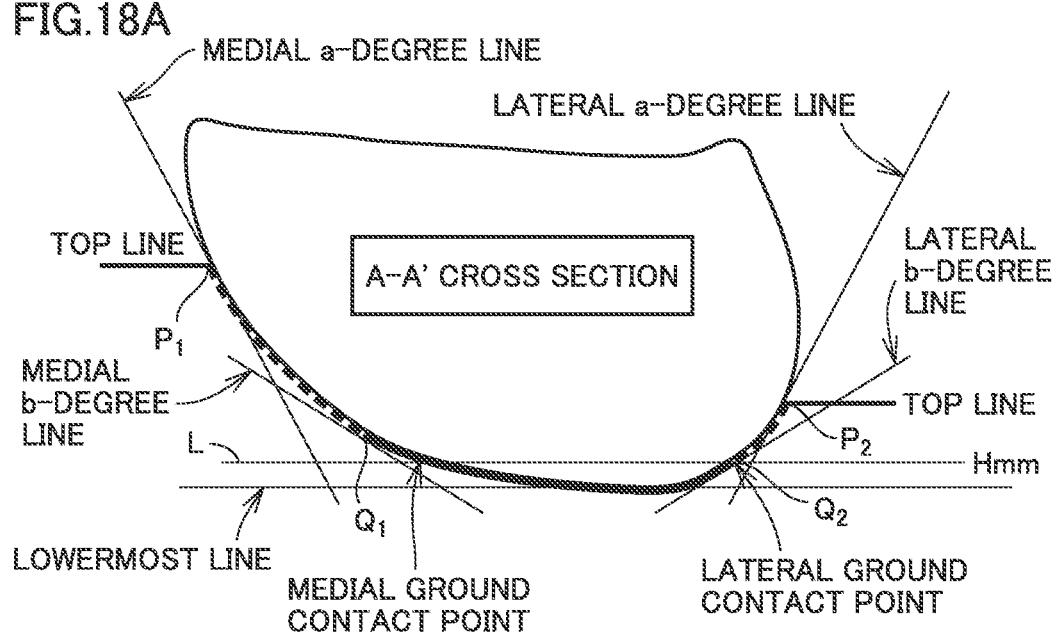

PREDICTION DEVICE, PREDICTION METHOD, AND PREDICTION SYSTEM

This nonprovisional application is based on Japanese Patent Application No. 2021-209086 filed on Dec. 23, 2021 with the Japan Patent Office, the entire contents of which are hereby incorporated by reference.

BACKGROUND OF THE INVENTION

Field of the Invention

The present disclosure relates to a prediction device, a prediction method, and a prediction system that predict a shape of a foot of a measurement subject person in an unloaded state.

Description of the Background Art

Custom-made shoes or shoe insoles (insoles) adapted to the shape of an individual's foot are generally produced based on the shape of the foot, in particular the shape of a sole of the foot. The shape of the foot is different between a loaded state in which a load is applied to the sole and an unloaded state in which no load is applied to the sole. For example, the shape of the foot in the unloaded state makes it possible to make a shoe or a shoe insole more suitable for the shape of the foot than the shape of the foot in the loaded state, since there is no deformation of the foot due to the load.

A known method for measuring a foot in an unloaded state is a method in which a plaster bandage (plaster) is wrapped around the foot of a measurement subject person with the measurement subject person placed on a bed, and then plaster is poured into the cured plaster bandage to take a mold of the shape of the foot. However, the method for measuring the shape of the foot using the plaster bandage needs to be performed by an expert with skills, and the time required for taking a mold tends to be long. In addition, a bed for taking a mold and a space for handling a gypsum are also required. For this reason, it is difficult to measure the shape of the foot using a plaster bandage in a store such as a shoe shop.

In this regard, Japanese Patent No. 5717894 discloses a method for acquiring data in a pressurized state, which is measurement data of a shape of a foot of a measurement subject person standing on a transparent plate, and data in a non-pressurized state, which is measurement data of a shape of the foot of the measurement subject person lightly in contact with the transparent plate, and producing a shoe insole based on a difference between the data in the pressurized state and the data in the non-pressurized state.

SUMMARY OF THE INVENTION

According to the method disclosed in Japanese Patent No. 5717894, a shoe insole suitable for the shape of the foot of the measurement subject person can be produced based on the shape of the foot of the measurement subject person in an unloaded state and the shape of the foot of the measurement subject person in a loaded state. However, in the method disclosed in Japanese Patent No. 5717894, it is necessary to measure the shape of the foot of the measurement subject person in both the unloaded state and the loaded state in the store, and thus the time required for the measurement tends to be long. Furthermore, in the method disclosed in Japanese Patent No. 5717894, since the measurement subject person needs to maintain a state where the measurement subject person lightly touches the transparent plate with a sole so as not to apply a load to the sole as much as possible, it is difficult to obtain accurate measurement data, and a salesclerk as a measurer also needs expert skills.

The present disclosure has been made in order to solve such a problem, and an object of the present disclosure is to provide a technique with which a shape of a foot of a measurement subject person in an unloaded state can be easily acquired.

A prediction device according to an aspect of the present disclosure includes: an acquisition unit that acquires measurement subject data including measurement data of a shape of a foot of a measurement subject person in a loaded state; a storage unit that stores first sample data in the loaded state and second sample data in an unloaded state, the first sample data and the second sample data being calculated from measurement data of foot shapes of a plurality of samples, the samples being identical both in the loaded state and the unloaded state; and a prediction unit that predicts the shape of the foot of the measurement subject person in the unloaded state. The prediction unit calculates a difference between the measurement subject data and the first sample data, and predicts the shape of the foot of the measurement subject person in the unloaded state based on the difference and the second sample data.

A prediction method according to an aspect of the present disclosure includes: acquiring measurement subject data including measurement data of a shape of a foot of a measurement subject person in a loaded state; storing first sample data in the loaded state and second sample data in an unloaded state, the first sample data and the second sample data being calculated from measurement data of foot shapes of a plurality of samples, the samples being identical both in the loaded state and the unloaded state; and predicting the shape of the foot of the measurement subject person in the unloaded state. The predicting includes: calculating a difference between the measurement subject data and the first sample data, and predicting the shape of the foot of the measurement subject person in the unloaded state based on the difference and the second sample data.

A prediction system according to an aspect of the present disclosure includes: a measurement device that measures a shape of a foot of a measurement subject person in a loaded state; and a prediction device that predicts the shape of the foot of the measurement subject person in an unloaded state. The prediction device includes: an acquisition unit that acquires measurement subject data from a measurement device, the measurement subject data including measurement data of a shape of a foot of a measurement subject person in a loaded state; a storage unit that stores first sample data in the loaded state and second sample data in an unloaded state, the first sample data and the second sample data being calculated from measurement data of foot shapes of a plurality of samples, the samples being identical both in the loaded state and the unloaded state; and a prediction unit that predicts the shape of the foot of the measurement subject person in the unloaded state. The prediction unit calculates a difference between the measurement subject data and the first sample data, and predicts the shape of the foot of the measurement subject person in the unloaded state based on the difference and the second sample data.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a schematic diagram illustrating a configuration of a prediction system according to an embodiment.

FIGS. 2A and 2B are diagrams respectively illustrating a shape of a foot in an unloaded state and a shape of the foot in a loaded state.

FIGS. 3A to 3H are diagrams for describing measurement items of the shape of the foot.

FIG. 9 is a diagram illustrating an example of loaded foot shape data stored in the prediction device.

FIG. 10 is a diagram illustrating an example of acquisition of loaded foot shape data.

FIGS. 11A and 11B are diagrams for explaining a reference foot length and an orthogonal foot width.

FIG. 12 is a diagram illustrating an example of unloaded foot shape data stored in the prediction device.

FIG. 13 is a diagram illustrating an example of acquisition of unloaded foot shape data.

FIGS. 18A to 18C are diagrams for explaining the change of second sample data based on an apparent arch.

DESCRIPTION OF THE PREFERRED EMBODIMENT

Figure 2A:
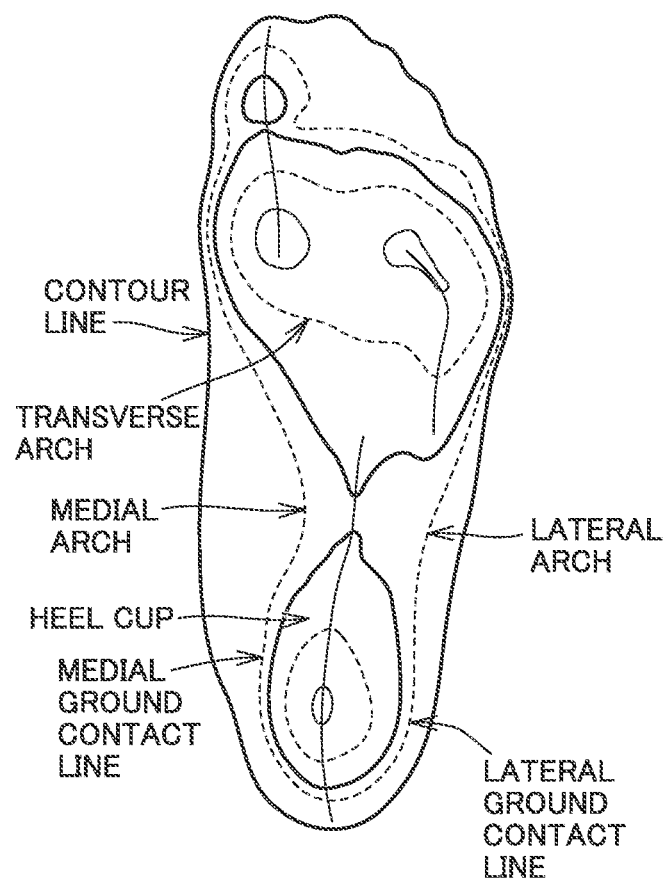

Hereinafter, an embodiment will be described with reference to the drawings. In the following description, the same components are denoted by the same reference numerals. Names and functions of such components are also the same. Therefore, detailed descriptions of these components will not be repeated.

[Configuration of prediction system]

FIG. 1 is a schematic diagram illustrating a configuration of a prediction system 100 according to an embodiment. In a store such as a shoe shop, custom made shoes or shoe insoles adapted to the shape of an individual's foot are produced. Since the shape of the foot in an unloaded state is not deformed by a load, it is possible to produce a shoe or a shoe insole more suitable for the shape of the foot than a shape of the foot in a loaded state.

For example, FIGS. 2A and 2B are diagrams illustrating a shape of a foot in the unloaded state and the shape of a foot in the loaded state. As illustrated in FIG. 2A, on a sole in the unloaded state, lines such as a contour line, a medial ground contact line, and a lateral ground contact line, arches such as a transverse arch, a medial arch, and a lateral arch, and a heel cup appear relatively clearly.

The contour line is a line indicating an outer shape of the foot. The medial ground contact line is a ground contact line that appears on a medial side of the foot that is a side of the first toe. The lateral ground contact line is a ground contact line that appears on a lateral side of the foot that is a side of the fifth toe. The medial arch is an arch formed from a heel bone to a first metatarsal bone. The lateral arch is an arch formed from the heel bone to a fifth metatarsal bone. The transverse arch is an arch formed between the medial arch and the lateral arch. The heel cup has a shape that appears on the heel portion of the sole. These portions of the sole have a role of alleviating impact during running and improving balance ability during standing.

On the other hand, as illustrated in FIG. 2B, in the sole in the loaded state, while the contour line, the medial ground contact line, and the lateral ground contact line can be determined, it is difficult to determine the transverse arch, the medial arch, the lateral arch, and the heel cup.

In the present disclosure, the "loaded state" means a state that can affect the determination of the arches of the sole and the heel cup, and includes, for example, a state in which the foot of the measurement subject person is in contact with the ground as illustrated in FIG. 1 and FIG. 10(A) to be described later. On the other hand, in the present disclosure, the "unloaded state" means a state that does not affect the determination of the arches of the sole and the heel cup, and includes, for example, a state in which the foot of the measurement subject person is not in contact with the ground as illustrated in FIG. 13(A) to be described later. It should be noted that the "unloaded state" may be a state in which a part of the foot of the measurement subject person is in contact with the ground or some object as long as it does not affect the determination of the arches of the sole and the heel cup.

In order to produce a shoe or a shoe insole suitable for the shape of the foot as described above, it is preferable to acquire the shape of the foot in the unloaded state. However, in a case where the shape of the foot in the unloaded state is acquired in a store, for example, it is necessary to perform an operation of winding a plaster bandage around the foot of the measurement subject person and casting the plaster into the cured plaster bandage to take a mold of the shape of the foot, and time required for the measurement tends to be long, and skills of the measurer is also required. Therefore, the prediction system 100 according to the embodiment is configured so that the shape of the foot of the measurement subject person in the unloaded state can be easily acquired.

As illustrated in FIG. 1, the prediction system 100 includes a measurement device 2 and a prediction device 1. While in the embodiment, an example of generating data for producing a shoe insole using the prediction system 100 is shown, the technology of the present disclosure may be applied to an example of generating data for producing a tailor-made shoe using the prediction system 100.

The measurement device 2 is, for example, a three-dimensional foot type scanner by laser measurement, and includes a top plate 21 and a laser measurement unit 22 installed so as to sandwich the top plate. When the measurement subject person places his/her foot on the top plate 21 in the standing posture, a load is applied to the top plate 21 from the foot by the weight of the measurement subject person. That is, a load is applied to the foot of the measurement subject person. The measurement device 2 measures the shape of the foot by the laser measurement unit 22 moving from the toe to the heel of the foot in a state in which a load is applied to the foot of the measurement subject person. The measurement device 2 outputs measurement subject data including measurement data (3D data) of the shape of the foot of the measurement subject person acquired by the laser measurement unit 22 to the prediction device 1. The measurement subject data only needs to include at least measurement data of the shape of the foot acquired by the measurement device 2, and may also include other data (for example, personal data such as gender or age of the measurement subject person).

The prediction device 1 acquires the measurement subject data from the measurement device 2, and predicts the shape of the foot of the measurement subject person in the unloaded state based on the measurement subject data. The prediction of the shape of the foot of the measurement subject person in the unloaded state by the prediction device 1 will be described later in detail. The prediction device 1 outputs the predicted data of the shape of the foot of the measurement subject person in the unloaded state to a 3D printer 3 or the like that produces the shoe insole.

As described above, in the prediction system 100, the prediction device 1 can predict the shape of the foot of the measurement subject person in the unloaded state based on the shape of the foot of the measurement subject person in the loaded state acquired by the measurement device 2. As a result, a user of the prediction system 100 can easily acquire the shape of the foot of the measurement subject person in the unloaded state.

[Measurement items of shape of foot]

With reference to FIGS. 3A to 3H, measurement items of the shape of the foot by the measurement device 2 will be described. FIGS. 3A to 3H are diagrams for describing measurement items of the shape of the foot. As shown in FIGS. 3A to 3H, the measurement items of the shape of the foot include a foot length, a ball girth, an orthogonal foot width, a heel width, a foot height, a first toe side angle, a heel angle, and an arch height.

Figure 3A:
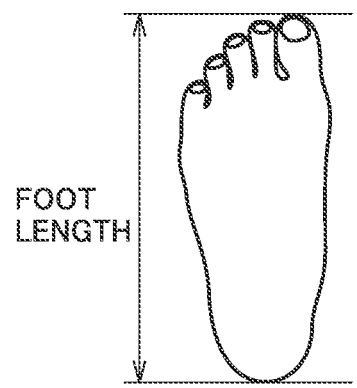
Figure 3B:
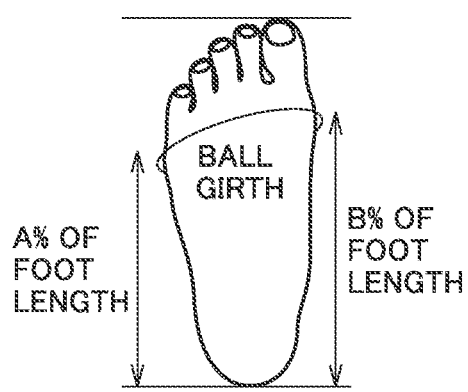

As shown in FIG. 3A, the foot length is a length from a back end of the heel to a tip of a longest finger. As illustrated in FIG. 3B, the ball girth is a length around the foot between a position on the side of the fifth toe at A % of the foot length starting from the rear end of the heel (for example, the base of the fifth toe) and a position on the side of the first toe at B % of the foot length starting from the rear end of the heel (for example, the base of the first toe). As illustrated in FIG. 3C, the orthogonal foot width is a length of the foot in the width direction between a position on the side of the fifth toe at C % of the foot length starting from the rear end of the heel (for example, the base of the fifth toe) and a position on the side of the first toe at D % of the foot length starting from the rear end of the heel (for example, the base of the first toe). Note that A to D are values greater than 0, and may be determined in advance according to a standard or the like, or may be arbitrarily set. Further, A may take the same value as C, and B may take the same value as D.

Figure 3D:
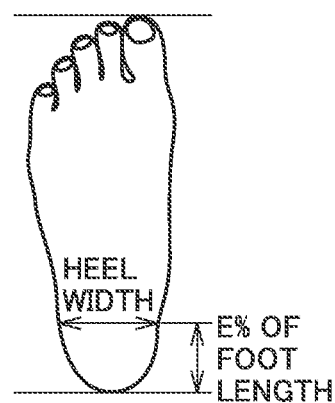
Figure 3E:
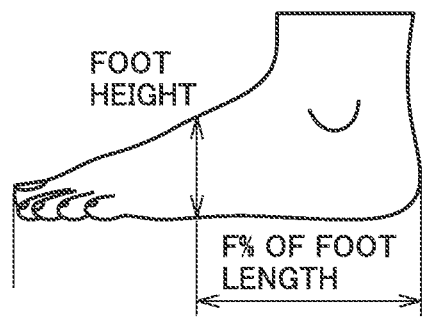
Figure 3F:
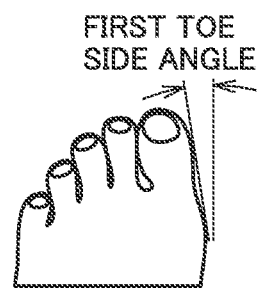
Figure 3G:
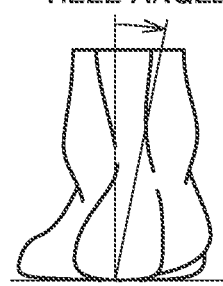
Figure 3H:
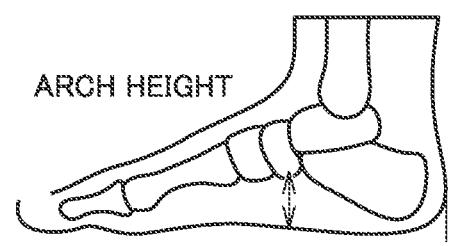

As illustrated in FIG. 3D, the heel width is a length of the heel in the width direction between a position on the side of the fifth toe at E % of the foot length starting from the rear end of the heel and a position on the side of the first toe at E % of the foot length starting from the rear end of the heel. As illustrated in FIG. 3E, the foot height is the height of the foot at a position at F % of the foot length starting from the rear end of the heel. As illustrated in FIG. 3F, the first toe side angle is an angle at which the first toe is inclined on the fifth toe side. As illustrated in FIG. 3G, the heel angle is an angle at which the heel is inclined with respect to a direction perpendicular to the ground. As illustrated in FIG. 3H, the arch height is the height from the ground to a navicular bone. The arch height may be calculated using a calculation formula based on the foot length, the ball girth, the heel width, the foot height, the first toe side angle, and the heel angle. Note that E and F are values greater than 0, and may be determined in advance according to a standard or the like, or may be arbitrarily set.

[Degree of bending of foot]

Figure 4:
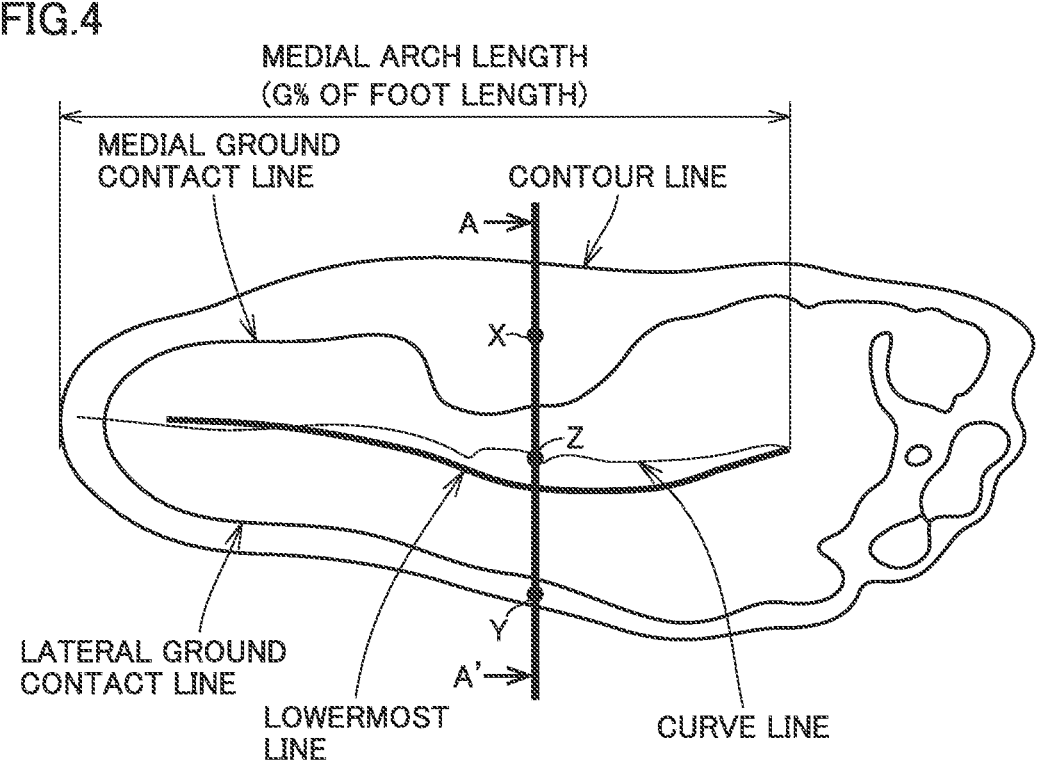
FIG. 4 is a diagram for describing a curve line of the foot.
Figure 5:
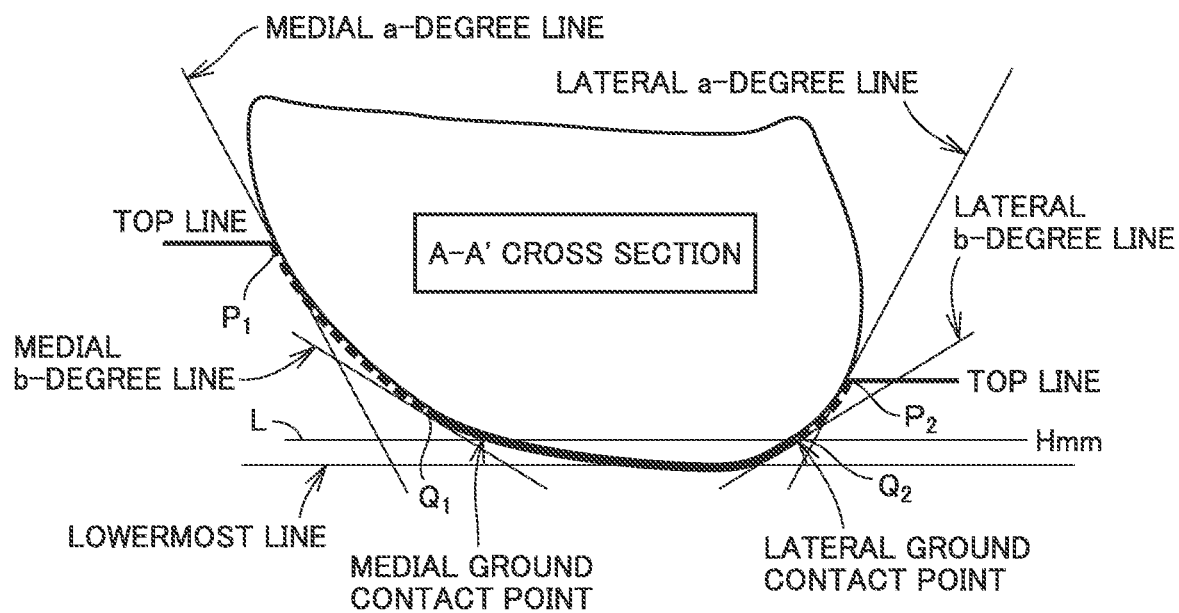
FIG. 5 is a view illustrating a cross section of the foot.

With reference to FIGS. 4 and 5, a degree of bending of the foot will be described. FIG. 4 is a diagram for describing a curve line of the foot. FIG. 5 is a view illustrating a cross section of the foot. As shown in FIG. 4, the curve line of the foot is defined in a range of the medial arch length corresponding to a length of G % of the foot length starting from the rear end of the heel, and is a line indicating the degree of bending of the foot. Note that G is a value greater than 0, and is set to a predetermined value within a range of 70% to 75%, for example. The value of G may be determined in advance according to a standard or the like, or may be arbitrarily set.

Assuming that a midpoint between the contour line and the medial ground contact line is X and a midpoint between the contour line and the lateral ground contact line is Y, a line passing through a midpoint Z between the point X and the point Y is the curve line.

FIG. 5 shows an A-A' cross section of the foot illustrated in FIG. 4. Note that FIG. 5 illustrates a cross section of the foot acquired in an unloaded state. As illustrated in FIG. 5, when a line passing through a portion of the foot in contact with the ground is defined as a lowermost line, a medial ground contact point can be represented by an intersection of a line L passing through a height of H mm from the lowermost line and the outer shape of the foot on the medial side. Since such a medial ground contact point is set for each cross section, lines connecting the plurality of medial ground contact points set in each of the plurality of cross sections in the foot length direction substantially coincide with the medial ground contact line illustrated in FIG. 4. Further, the lateral ground contact point can be expressed by an intersection of the line L and the outer shape of the foot on the lateral side. Since such a lateral ground contact point is set for each cross section, lines connecting the plurality of lateral ground contact points set in each of the plurality of cross sections in the foot length direction substantially coincide with the lateral ground contact line illustrated in FIG. 4. Note that H is a value greater than 0, and may be determined in advance according to a standard or the like, or may be arbitrarily set.

A contact point $P_1$ between a line inclined by a degrees from the ground toward the medial side of the foot (medial a-degree line) and the outer shape on the medial side of the foot becomes a part of the top line of the shoe insole on the medial side of the foot. In addition, a contact point $P_2$ between a line inclined by a degrees from the ground toward the lateral side of the foot (lateral a-degree line) and the outer shape on the lateral side of the foot becomes a part of the top line of the shoe insole on the lateral side of the foot. Note that a is a value greater than 0, and is set to a predetermined value within a range of 45 degrees to 65 degrees, for example. The value of a may be determined in advance according to a standard or the like, or may be arbitrarily set.

In addition, a contact point between a line inclined by b degrees from the ground toward the medial side of the foot (medial b-degree line) and the outer shape on the medial side of the foot is $Q_1$, and a contact point between a line inclined by b degrees from the ground toward the lateral side of the foot (lateral a-degree line) and the outer shape on the lateral side of the foot is $Q_2$. Note that b is a value greater than 0, and is set to a predetermined value within a range of 15 degrees to 30 degrees, for example. The value of b may be determined in advance according to a standard or the like, or may be arbitrarily set.

A portion of the outer shape on an upper side of the foot formed from the contact point $P_1$ to the contact point $P_2$ is also referred to as an instep portion. A portion of the outer shape on a lower side of the foot formed from the contact point $P_1$ to the contact point $Q_1$ is also referred to as a medial windlass portion. A portion of the outer shape on the lower side of the foot formed from the contact point $P_2$ to the contact point $Q_2$ is also referred to as a lateral windlass portion. A portion of the outer shape on the lower side of the foot formed from the contact point $Q_1$ to the contact point $Q_2$ is also referred to as a bottom portion.

[Foot shape data]

Figure 6:
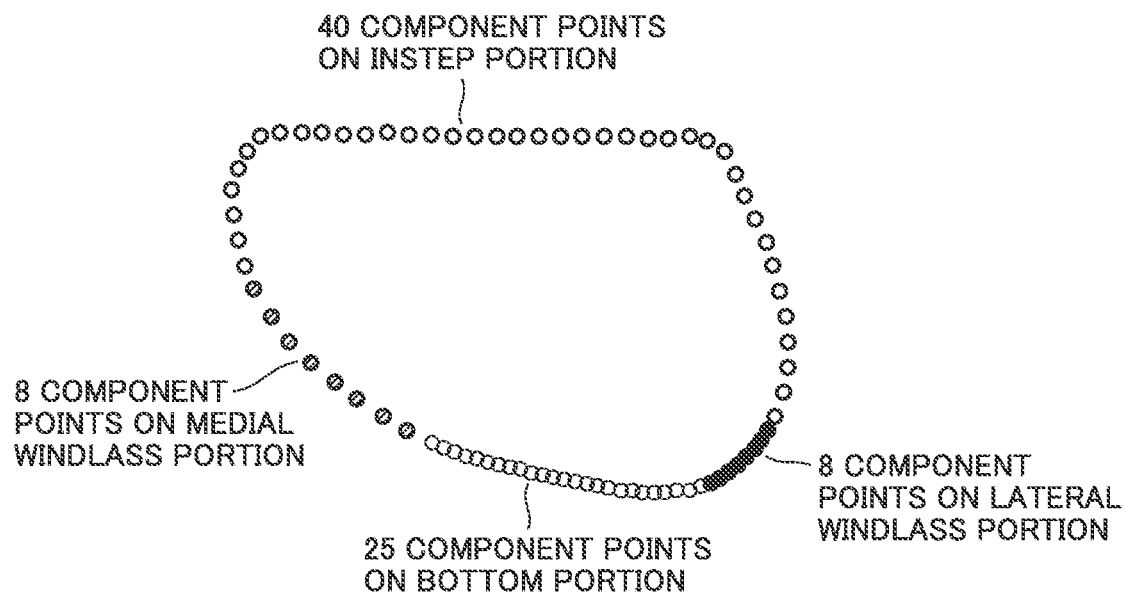
FIG. 6 is a diagram for describing foot shape data.

With reference to FIG. 6, data of the shape of the foot used when preparing the shoe insole will be described. FIG. 6 is a diagram for describing the foot shape data. As illustrated in FIG. 6, the foot shape data includes position data of each of a plurality of component points arranged along the outer shape of the cross section of the foot.

For example, in the example of FIG. 6, the shape data includes, in the cross section of the foot, 25 component points obtained by equally dividing the bottom portion into 25 parts, 8 component points obtained by equally dividing the medial windlass portion into 8 parts, 8 component points obtained by equally dividing the lateral windlass portion into 8 parts, and 40 component points obtained by equally dividing the instep portion into 40 parts.

In the shape data, the plurality of component points (81 points in the example of FIG. 6) arranged in the cross section are provided in the foot length direction at predetermined intervals (for example, every 1 mm). That is, in the case of a foot having a foot length of 255 mm, the shape data includes position data of each of the 81 component points arranged respectively for the 255 cross sections. The number of component points of each of the bottom portion, the medial windlass portion, the lateral windlass portion, and the instep portion is not limited to the above-described number, and can be arbitrarily set.

[Homology model]

Figure 7:
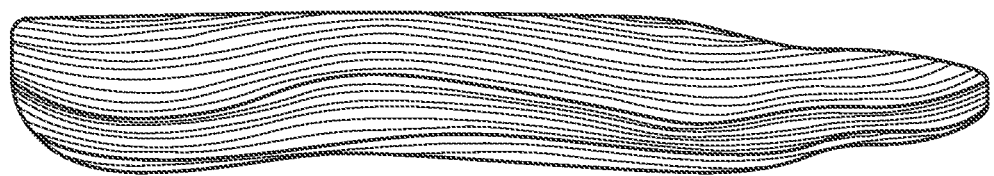
FIG. 7 is a diagram for describing a homology model.

With reference to FIG. 7, a homology model will be described. FIG. 7 is a diagram for describing the homology model. As illustrated in FIG. 7, the homology model is a foot-shape model representing the shape of the foot using a plurality of lines. Specifically, 81 lines in the foot length direction can be formed by connecting the respective component points of the bottom portion, the medial windlass portion, the lateral windlass portion, and the instep portion obtained for each cross section of the foot as illustrated in FIG. 6 in the foot length direction. With such 81 lines, the homology model can be obtained. For example, in the case of the foot having the foot length of 255 mm, a homology model including 20655 (255×81) component points (position data) can be created.

[Configuration of prediction device]

Figure 8:
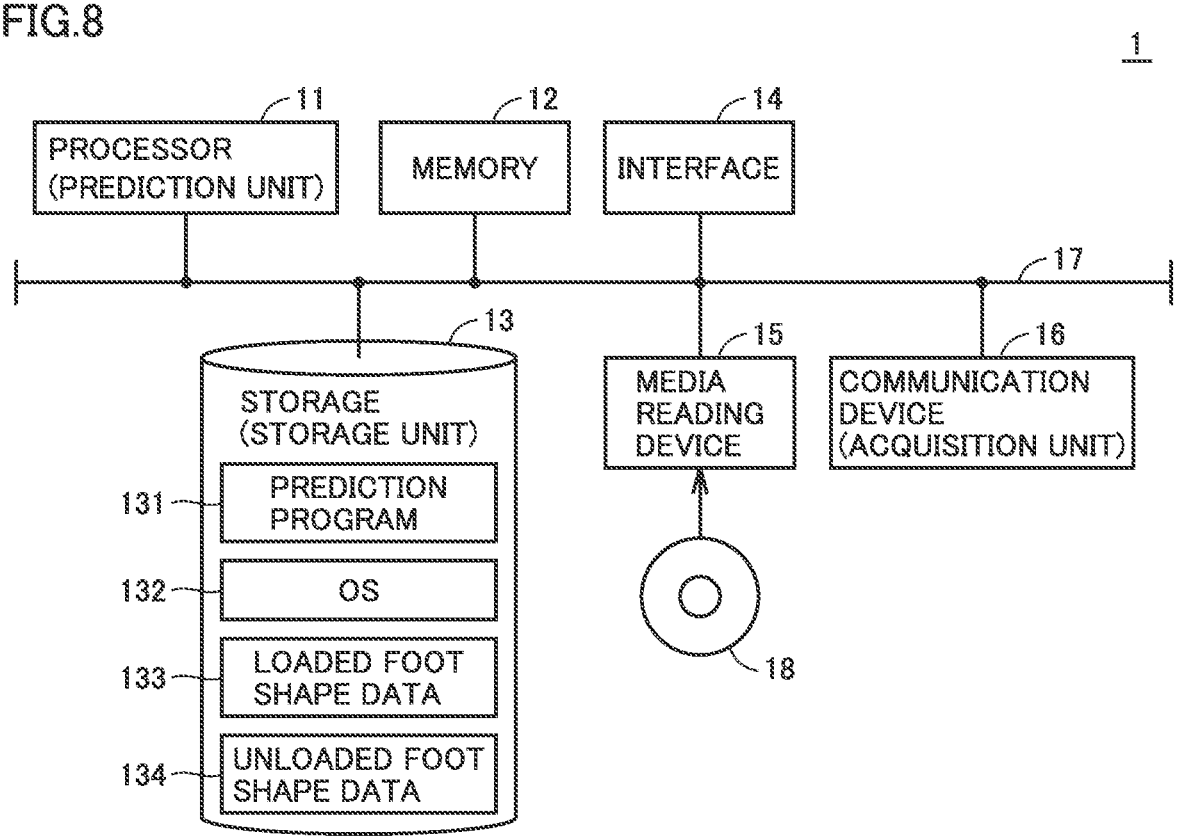
FIG. 8 is a block diagram illustrating a configuration of a prediction device according to the embodiment.

FIG. 8 is a block diagram illustrating a configuration of the prediction device 1 according to the embodiment. As illustrated in FIG. 8, the prediction device 1 includes a processor 11, a memory 12, a storage 13, an interface 14, a medium reading device 15, and a communication device 16. These components are connected via a processor bus 17.

The processor 11 is an example of a "prediction unit". The processor 11 is a computer that reads a program (for example, an operating system (OS) 132 and a prediction program 131) stored in the storage 13, decompresses the read program in the memory 12, and executes the program.

The processor 11 includes, for example, a central processing unit (CPU), a graphics processing unit (GPU), a multi processing unit (MPU), or the like. Note that while the processor 11 has a function of executing various processes by executing a program, some or all of these functions may be implemented using a dedicated hardware circuit such as an application specific integrated circuit (ASIC) or a field-programmable gate array (FPGA). The "processor" is not limited to a processor in a narrow sense that executes processing in a stored program system such as a CPU or an MPU, and may include a hardwired circuit such as an ASIC or an FPGA. Therefore, the processor may be configured by processing circuitry whose processing is predefined by computer-readable code and/or hardwired circuitry.

The memory 12 includes a volatile memory such as a dynamic random access memory (DRAM) or a static random access memory (SRAM), a nonvolatile memory such as a read only memory (ROM) or a flash memory, or the like.

The storage 13 is an example of a "storage unit". The storage 13 includes, for example, a nonvolatile storage device such as a hard disk drive (HDD) or a solid state drive (SSD). The storage 13 stores the prediction program 131, the OS 132, loaded foot shape data 133, and unloaded foot shape data 134.

The prediction program 131 is a program for causing the prediction device 1 to execute processing of predicting the shape of the foot of the measurement subject person in the unloaded state (prediction process illustrated in FIG. 14 to be described later) based on the shape of the foot of the measurement subject person in the loaded state acquired by the measurement device 2.

The loaded foot shape data 133 is an example of "first sample data". The loaded foot shape data 133 includes data calculated from the measurement data of the foot shapes of the plurality of samples in the loaded state. The loaded foot shape data 133 will be described later with reference to FIGS. 9 to 11B.

The unloaded foot shape data 134 is an example of "second sample data". The unloaded foot shape data 134 includes data calculated from the measurement data of the foot shapes of the plurality of samples in the unloaded state. The unloaded foot shape data 134 will be described later with reference to FIGS. 12 and 13.

The interface 14 receives an input by the user of the prediction device 1, and includes a keyboard, a mouse, a touch device, and the like.

The medium reading device 15 receives a storage medium such as the removable disk 18 and acquires data stored in the removable disk 18.

The communication device 16 is an example of an "acquisition unit". The communication device 16 transmits and receives data to and from other devices by performing wired communication or wireless communication. For example, the communication device 16 communicates with the measurement device 2 to acquire the measurement data of the shape of the foot acquired by the measurement device 2 from the measurement device 2. The communication device 16 outputs the foot shape data used to produce the shoe insole to the 3D printer 3 by communicating with the 3D printer 3.

Note that acquisition of the measurement data of the shape of the foot by the prediction device 1 is not limited to acquisition of the measurement data from the measurement device 2 by the communication device 16. For example, the prediction device 1 may acquire the measurement data of the shape of the foot that is input by the user using the interface 14. In this case, the interface 14 is an example of an "acquisition unit". Alternatively, the prediction device 1 may read the measurement data of the shape of the foot stored in the removable disk 18 by the medium reading device 15. In this case, the medium reading device 15 is an example of an "acquisition unit".

[Loaded foot shape data]

With reference to FIGS. 9 to 11B, the loaded foot shape data 133 will be described. FIG. 9 is a diagram illustrating an example of the loaded foot shape data stored in the prediction device 1. FIG. 10 is a diagram illustrating an example of acquisition of the loaded foot shape data. FIGS. 11A and 11B are diagrams for explaining a reference foot length and an orthogonal foot width.

As illustrated in FIG. 9, the loaded foot shape data includes data obtained by classifying the measurement data of the foot shapes of the plurality of samples in the loaded state (specifically, a homology model created based on the measurement data) according to a plurality of foot shape types based on at least one feature amount related to the shape of the foot. In the example illustrated in FIG. 9, the foot arch height ratio and the heel angle (the angle of the heel inclined on the medial side) are used as the at least one feature amount. Further, the loaded foot shape data is classified into a total of nine foot shape types by three arch types classified based on the foot arch height ratio and three heel angle types classified based on the heel angle.

The arch types are classified by the foot arch height ratio calculated by dividing the arch height (FIG. 3H) by the foot length (FIG. 3A). If the foot arch height ratio of the foot of the sample is less than $A_1$ %, the foot of the sample is classified as flat. If the foot arch height ratio of the foot of the sample is greater than or equal to $A_1$ % or less than $A_2$ %, the foot of the sample is classified as average. If the foot arch height ratio of the foot of the sample is greater than or equal to $A_2$ %, the foot of the sample is classified as high arch. Here, $A_1$ and $A_2$ are values greater than 0 ($0<A_1<A_2$), and for example, $A_1$ is set to a predetermined value within a range of 12% to 16%, and $A_2$ is set to a predetermined value within a range of 18% to 22%. The values of $A_1$ and $A_2$ may be determined in advance according to a standard or the like, or may be arbitrarily set.

The heel angle types are calculated based on the heel angle (FIG. 3G). If the heel angle of the foot of the sample is less than $B_1$ degrees, the foot of the sample is classified as varus. If the heel angle of the foot of the sample is greater than or equal to $B_1$ degrees and less than $B_2$ degrees, the foot of the sample is classified as average. If the heel angle of the foot of the sample is greater than or equal to $B_2$ degrees, the foot of the sample is classified as valgus. For example, $B_1$ is set to a predetermined value within a range of −2 degrees to 0 degrees, and $B_2$ is set to a predetermined value within a range of 2 degrees to 5 degrees. The values of $B_1$ and $B_2$ may be determined in advance according to a standard or the like, or may be arbitrarily set.

In the generation of the loaded foot shape data, as illustrated in FIG. 10(A), first, the shape of the foot of each of the plurality of sample subjects in the loaded state is acquired by the measurement device 2. The method for measuring the foot of the sample subject by the measurement device 2 is the same as the method for measuring the foot of the measurement subject person by the measurement device 2 illustrated in FIG. 1. Specifically, when the sample subject places his/her foot on the top plate 21 in the standing posture, a load is applied to the top plate 21 from the foot by the weight of the sample subject. The measurement device 2 measures the shape of the foot by the laser measurement unit 22 moving from the toe to the heel of the foot in a state in which a load is applied to the foot of the sample subject.

As illustrated in FIG. 10(B), the measurement data of the shape of the foot of the sample acquired by the measurement device 2 is classified according to the plurality of foot shape types based on the at least one feature amount (in this example, the foot arch height ratio and the heel angle) related to the shape of the foot of the sample. Specifically, a homology model as illustrated in FIG. 7 is created based on the measurement data of the shape of the foot of the sample acquired by the measurement device 2, and the created homology model is classified according to the plurality of foot shape types.

The homology model of the foot of the sample classified according to the plurality of foot shape type is changed to match the reference foot length and the orthogonal foot width.

The reference foot length and the orthogonal foot width will be described with reference to FIGS. 11A and 11B. As shown in FIG. 11A, the plurality of foot shape types may be set based on the arch types and the heel angle types. As illustrated in FIG. 11B, when the reference foot length is X mm (for example, 255 mm), the orthogonal foot width is determined in advance according to the foot shape type. Note that X and $Y_1$ to $Y_9$ are values greater than 0, and may be determined in advance according to a standard or the like, or may be arbitrarily set.

By changing the homology model of the foot of the sample according to the reference foot length and the orthogonal foot width, the curve line of the foot shown in FIG. 4 that can be calculated from the homology model (measurement data) is also changed.

Returning to FIG. 10, after the homology model of the shape of the foot of the sample is changed in accordance with the reference foot length and the orthogonal foot width, the average value of the homology models of the shapes of the feet of the samples after the change is calculated for each of the plurality of foot shape types. As illustrated in FIG. 10(C), the average value calculated for each of the plurality of foot shape types is included in the loaded foot shape data 133 as data A1 to A9.

As described above, the designer of the prediction device 1 acquires the sample data in the loaded state according to the plurality of foot shape types by classifying homology models created based on the measurement data of the shape of the foot of the sample acquired by the measurement device 2 according to the types based on the at least one feature amount (in this example, the foot arch height ratio and the heel angle), changing the classified homology models in accordance with the reference foot length and the orthogonal foot width, and calculating the average value from the changed homology model. The acquired sample data in the loaded state is stored in the storage 13 in advance as the loaded foot shape data 133 (first sample data). That is, the loaded foot shape data 133 (first sample data) stored in the storage 13 includes average foot shape data in the loaded state according to the plurality of foot shape types.

[Unloaded foot shape data]

With reference to FIGS. 12 and 13, the unloaded foot shape data 134 will be described. FIG. 12 is a diagram illustrating an example of unloaded foot shape data stored in the prediction device 1. FIG. 13 is a diagram illustrating an example of acquisition of the unloaded foot shape data.

As illustrated in FIG. 12, the unloaded foot shape data includes data obtained by classifying the measurement data of the foot shapes of the plurality of samples in the unloaded state (specifically, a homology model created based on the measurement data) according to a plurality of foot shape types based on at least one feature amount related to the shape of the foot. In the example illustrated in FIG. 12, the foot arch height ratio and the heel angle are used as the at least one feature amount. Further, the unloaded foot shape data is classified into a total of nine foot shape types by three arch types classified based on the foot arch height ratio and three heel angle types classified based on the heel angle.

In the generation of the unloaded foot shape data, as illustrated in FIG. 13(A), first, the shape of the foot of each of the plurality of sample subjects in the unloaded state is acquired using the plaster bandage. The plurality of sample subjects in the unloaded state are the same as the plurality of sample subjects in the loaded state in FIG. 10. In addition, by measuring the foot shape of the obtained gypsum with the measurement device 2, the shape of the foot of each of the plurality of sample subjects in the unloaded state is acquired.

As illustrated in FIG. 13(B), the measurement data of the shape of the foot of the sample acquired by using the plaster bandage is classified according to the plurality of foot shape types based on the at least one feature amount (in this example, the foot arch height ratio and the heel angle) related to the shape of the foot of the sample. Note that, since the plurality of sample subjects in the loaded state in FIG. 10 and the plurality of sample subjects in the unloaded state in FIG. 13 are the same, the measurement data of the shapes of the feet of the plurality of sample subjects in the unloaded state only needs to be classified according to the foot shape types into which the measurement data of the shapes of the feet of the plurality of sample subjects in the loaded state is classified. Specifically, a homology model as illustrated in FIG. 7 is created based on the measurement data of the shape of the foot of the sample acquired by the measurement device 2, and the created homology model is classified into the same foot shape type as the homology model of the foot of the sample subject in the loaded state.

The homology model of the foot of the sample classified according to the plurality of foot shape type is changed to match the reference foot length and the orthogonal foot width. The change of the homology model of the foot of the sample in the unloaded state is the same as the change of the homology model of the foot of the sample in the loaded state of FIG. 10.

By changing the homology model of the foot of the sample according to the reference foot length and the orthogonal foot width, the curve line of the foot shown in FIG. 4 that can be calculated from the homology model (measurement data) is also changed.

After the homology model of the foot of the sample is changed in accordance with the reference foot length and the orthogonal foot width, the average value of the homology models of the feet of the samples after the change is calculated for each of the plurality of foot shape types. As illustrated in FIG. 13(C), the average value calculated for each of the plurality of foot shape types is included in the unloaded foot shape data 134 as data B1 to B9.

As a result, the designer of the prediction device 1 acquires the sample data in the unloaded state according to the plurality of foot shape types by classifying homology models created based on the measurement data of the shape of the foot of the sample acquired using the plaster bandage according to the types based on the at least one feature amount (in this example, the foot arch height ratio and the heel angle), changing the classified homology models in accordance with the reference foot length and the orthogonal foot width, and calculating the average value from the changed homology model. The acquired sample data in the unloaded state is stored in the storage 13 in advance as the unloaded foot shape data 134 (second sample data). That is, the unloaded foot shape data 134 (second sample data) stored in the storage 13 includes the average foot shape data in the unloaded state according to the plurality of foot shape types.

[Prediction of shape of foot of measurement subject person]

Figure 14:
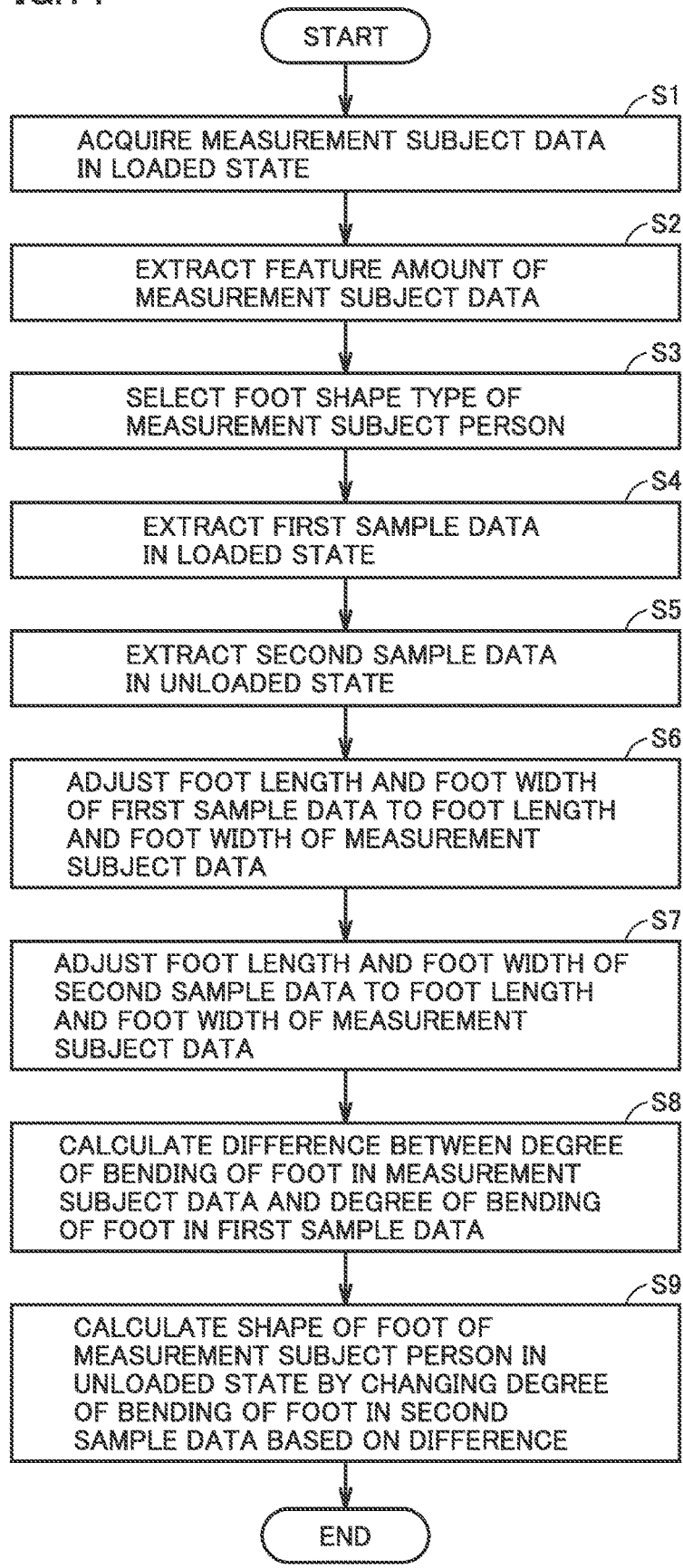
FIG. 14 is a flowchart showing a prediction process executed by the prediction device according to the embodiment.
Figure 15:
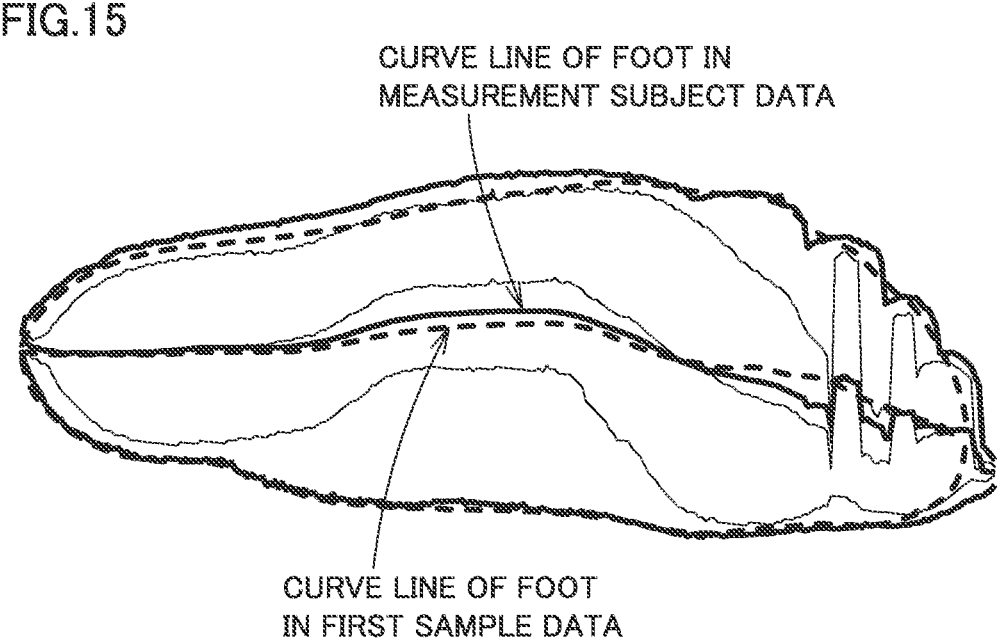
FIG. 15 is a diagram for describing calculation of a difference between measurement subject data and first sample data.
Figure 16:
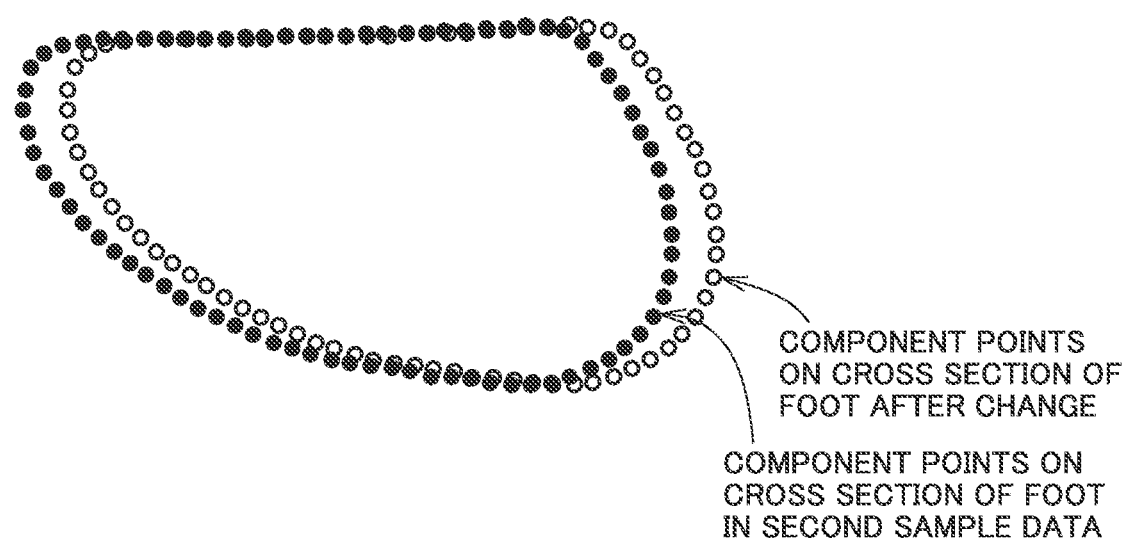
FIG. 16 is a diagram for explaining a change of the sample data based on the difference.

With reference to FIGS. 14 to 16, the prediction process of the shape of the foot of the measurement subject person in the unloaded state by the prediction device 1 will be described. FIG. 14 is a flowchart showing the prediction process executed by the prediction device 1 according to the embodiment. FIG. 15 is a diagram for describing calculation of a difference between the measurement subject data and the first sample data. FIG. 16 is a diagram for explaining the change of the second sample data based on the difference. Steps (hereinafter, indicated by "S") illustrated in FIG. 14 are realized by the processor 11 of the prediction device 1 executing the prediction program 131.

As illustrated in FIG. 14, the prediction device 1 acquires measurement subject data including the measurement data of the shape of the foot of the measurement subject person in the loaded state acquired by the measurement device 2 (S1). The prediction device 1 creates a homology model as illustrated in FIG. 7 based on the measurement subject data and extracts a feature amount of the measurement subject data (in this example, the foot arch height ratio and the heel angle) (S2). The prediction device 1 selects the foot shape type of the foot of the measurement subject person based on the feature amount of the measurement subject data (S3). For example, the prediction device 1 selects one of the foot shape types illustrated in FIG. 11A classified based on the arch type and the heel angle type of the foot of the measurement subject person.

The prediction device 1 extracts the first sample data in the loaded state suitable for the foot shape type of the measurement subject person selected in S3 from the loaded foot shape data 133 stored in the storage 13 (S4). The extracted first sample data includes the average foot shape data (homology model) in the loaded state suitable for the foot shape type of the measurement subject person.

Further, the prediction device 1 extracts the second sample data in the unloaded state suitable for the foot shape type of the measurement subject person selected in S3 from the unloaded foot shape data 134 stored in the storage 13 (S5). The extracted second sample data includes the average foot shape data (homology model) in the unloaded state suitable for the foot shape type of the measurement subject person.

The prediction device 1 adjusts the foot length and the orthogonal foot width of the first sample data in the loaded state extracted in S4 to the foot length and the orthogonal foot width of the homology model created based on the measurement subject data (S6). As a result, the curve line of the average foot in the loaded state corresponding to the first sample data is changed in accordance with the foot length and the orthogonal foot width of the measurement subject person.

Further, the prediction device 1 adjusts the foot length and the orthogonal foot width of the second sample data in the unloaded state extracted in S5 to the foot length and the orthogonal foot width of the homology model created based on the measurement subject data (S7). As a result, the curve line of the average foot in the unloaded state corresponding to the second sample data is changed in accordance with the foot length and the orthogonal foot width of the measurement subject person.

The prediction device 1 calculates a curve line of the foot based on each of the measurement subject data and the first sample data changed in S6, and calculates a difference between the curve line of the foot in the measurement subject data and the curve line of the foot in the loaded state corresponding to the first sample data changed in S6 (S8).

Specifically, as illustrated in FIG. 15, the prediction device 1 calculates the difference between the curve lines in the foot length direction by comparing the curve line of the foot in the measurement subject data represented by a solid line with the curve line of the foot in the loaded state corresponding to the first sample data represented by a dotted line.

Here, the curve line of the foot of the first sample data and the curve line of the foot of the measurement subject data in the loaded state only need to be calculated from the shape of the sole acquired by the measurement device 2. Specifically, since the contour line, the medial ground contact line, and the lateral ground contact line can be determined even in the loaded state as illustrated in FIGS. 2A and 2B, the curve line of the foot of the first sample data and the curve line of the foot of the measurement subject data in the loaded state only need to be calculated on the basis of the contour line, the medial ground contact line, and the lateral ground contact line as described with reference to FIG. 4. As the curve line of the foot of the first sample data, the curve line of the foot of the second sample data in the unloaded state may be used. For example, as described with reference to FIGS. 4 and 5, the medial ground contact line and the lateral ground contact line may be calculated using the intersection of the line L passing through the height of H mm from the lowermost line and the outer shape of the medial or lateral side of the foot, the curve line of the foot of the second sample data may be calculated using the calculated medial ground contact line and the lateral ground contact line, and the calculated curve line may be used as the curve line of the foot of the first sample data.

The prediction device 1 calculates the shape of the foot of the measurement subject person in the unloaded state (homology model) by changing the degree of bending of the foot (curve line) in the unloaded state corresponding to the second sample data changed in S6 based on the calculated difference between the curve lines (S9). Thereafter, the prediction device 1 ends this process.

Specifically, as illustrated in FIG. 16, the prediction device 1 moves the plurality of component points arranged along the outer shape of the cross section of the foot in the second sample data in a direction of offsetting the difference calculated in S8. That is, the prediction device 1 moves the plurality of component points arranged along the outer shape of the cross section of the foot in the second sample data so that the curve line of the foot in the second sample data matches the curve line of the foot in the measurement subject data. The prediction device 1 executes such movement of the plurality of component points at predetermined intervals (for example, every 1 mm) along the foot length direction.

As a result, the prediction device 1 can calculate data of the shape of the foot of the measurement subject person in the unloaded state (homology model) from the measurement data of the shape of the foot of the measurement subject person in the loaded state acquired by the measurement device 2.

[Production of shoe insole]

Figure 17:
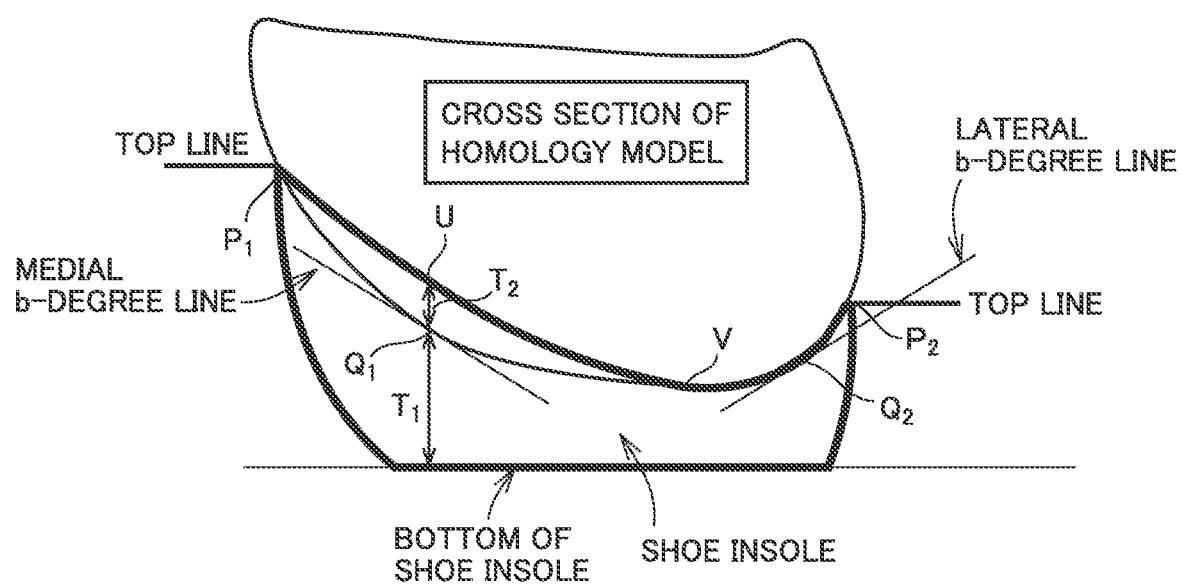
FIG. 17 is a view for illustrating an example of production of a shoe insole.

An example of production of the shoe insole will be described with reference to FIG. 17. FIG. 17 is a view for illustrating an example of the production of the shoe insole. FIG. 17 illustrates one cross section of the homology model representing the shape of the foot of the measurement subject person in the unloaded state acquired by the prediction device 1 through the prediction process of FIG. 14. In FIG. 17, similarly to FIG. 5, it is assumed that a partial point of the top line on the medial side of the homology model is $P_1$, a partial point of the top line on the lateral side of the homology model is $P_2$, a contact point between the medial b-degree line and the outer shape on the medial side of the homology model is $Q_1$, and a contact point between the lateral b-degree line and the outer shape on the lateral side of the homology model is $Q_2$.

The designer of the shoe insole measures a length $T_1$ of the contact point $Q_1$ with respect to the bottom surface of the shoe insole, and obtains a point U by adding a support adjustment amount $T_2$ to the length $T_1$. The designer can acquire a surface shape of the shoe insole in one cross section of the homology model by connecting the point $P_1$ on the top line on the medial side of the homology model, the point U, a lowest point V of the homology model, and the point $P_2$ on the top line on the lateral side of the homology model with a line. The designer can produce the shoe insole by performing such work for each of the plurality of cross sections in the foot length direction.

[Modified examples]

The present disclosure is not limited to the above embodiment, and various modifications and applications are possible. Hereinafter, modified examples applicable to the present disclosure will be described.

In the prediction process, the prediction device 1 according to the embodiment uses the measurement data of the shape of the foot of the measurement subject person measured in the standing posture as illustrated in FIG. 1 and the first sample data calculated from the measurement data of the shape of the foot of the sample subject measured in the standing posture as illustrated in FIG. 10. However, the prediction process is not limited to the process executed using the data measured in the standing posture.

For example, the prediction device 1 may execute the prediction process using the measurement data of the shape of the foot of the measurement subject person measured in the sitting posture and the first sample data calculated from the measurement data of the shape of the foot of the sample subject measured in the sitting posture.

The prediction device 1 according to the embodiment classifies the measurement subject data, the first sample data, and the second sample data based on the foot arch height ratio and the heel angle as the at least one feature amount, but classification of the data is not limited to the classification based on the foot arch height ratio and the heel angle.

For example, the prediction device 1 may classify the measurement subject data, the first sample data, and the second sample data based on at least one of the foot arch height ratio, the heel angle, the ball girth, the degree of bending of the foot (curve line), the shape of the toe, and the age as the at least one feature amount. All of these feature amounts are parameters that can affect the shape of the foot, and the prediction device 1 can accurately classify the measurement subject data, the first sample data, and the second sample data using any one of these feature amounts.

In the prediction system 100 according to the embodiment, the prediction device 1 may be installed in a store where the measurement device 2 is installed, or may exist as a cloud server device. Furthermore, the prediction device 1 existing as a cloud server device may be communicably connected to measurement devices 2 installed in a plurality of stores, and may predict the shape of the foot of a measurement subject person in the unloaded state based on the measurement subject data acquired from each of the measurement devices 2.

The prediction device 1 according to the embodiment adjusts the foot length and the orthogonal foot width of the first sample data in the loaded state to the foot length and the orthogonal foot width of the homology model created based on the measurement subject data in S6, and the foot length and the orthogonal foot width of the second sample data in the unloaded state to the foot length and the orthogonal foot width of the homology model created based on the measurement subject data in S7. However, the items to be adjusted may be other than the foot length and the orthogonal foot width.

For example, after adjusting the foot length and the orthogonal foot width of the first sample data in the loaded state to the foot length and the orthogonal foot width of the homology model created based on the measurement subject data in S6, the prediction device 1 may correct the changed first sample data based on the apparent arch length of the homology model in the measurement subject data. Further, after adjusting the foot length and the orthogonal foot width of the second sample data in the unloaded state to the foot length and the orthogonal foot width of the measurement subject data in S7, the prediction device 1 may correct the changed second sample data based on the apparent arch length of the homology model in the measurement subject data.

Figure 18B:
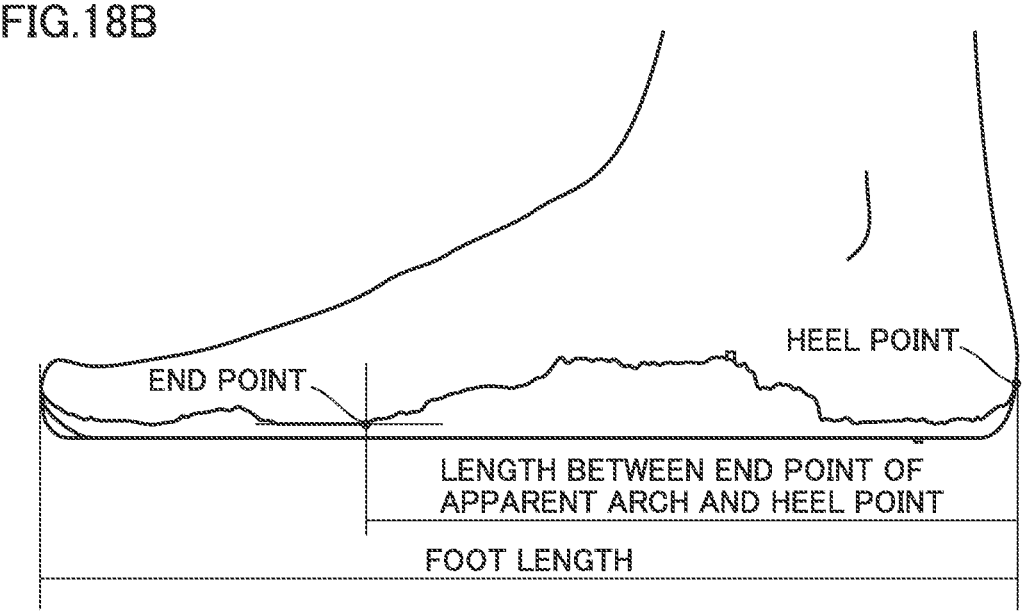
Figure 18C:
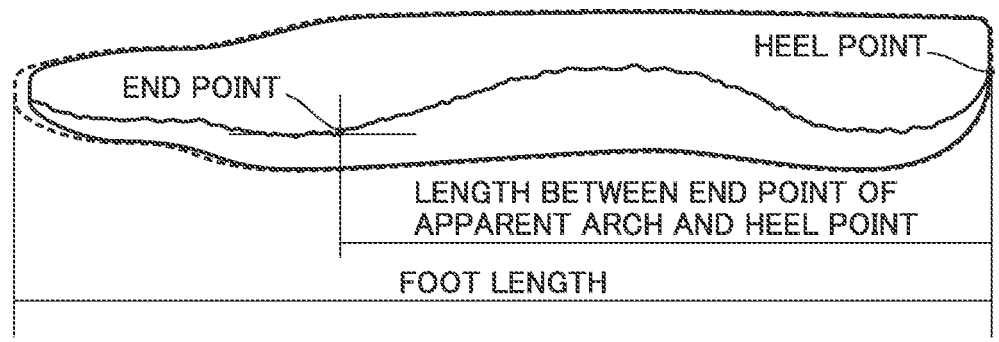

For example, FIGS. 18A to 18C are diagrams for explaining the change of the sample data based on the apparent arch. As illustrated in FIG. 18A, in the cross section of the foot, a contact point between a line inclined a degrees from the ground toward the medial side of the foot (medial a-degree line) and the outer shape on the medial side of the foot is assumed to be $P_1$. As illustrated in FIG. 18B, contact points $P_1$ are acquired at predetermined intervals (for example, every 1 mm) in the foot length direction, and a line connecting the plurality of acquired contact points $P_1$ is defined as an apparent arch. Then, the length between an end point of the apparent arch and a heel point where the heel is located is defined as an apparent arch length.

By adjusting the foot length and the orthogonal foot width of the first sample data in the loaded state to the foot length and the orthogonal foot width of the homology model created based on the measurement subject data in S6, the prediction device 1 changes the curve line of the average foot in the loaded state corresponding to the first sample data in accordance with the foot length and the orthogonal foot width of the measurement subject person. Further, the prediction device 1 corrects the curve line of the foot in the first sample data by adjusting the apparent arch length in the first sample data after the change to the apparent arch length of the homology model in the measurement subject data.

Moreover, by adjusting the foot length and the orthogonal foot width of the second sample data in the unloaded state to the foot length and the orthogonal foot width of the homology model created based on the measurement subject data in S7, the prediction device 1 changes the curve line of the average foot in the unloaded state corresponding to the second sample data in accordance with the foot length and the orthogonal foot width of the measurement subject person. Further, the prediction device 1 corrects the curve line of the foot in the second sample data by adjusting the apparent arch length in the second sample data after the change to the apparent arch length of the homology model in the measurement subject data.

By performing such correction, as illustrated in FIG. 18C, the prediction device 1 can adjust the foot length of the sample data before correction represented by a dotted line to the foot length of the sample data after correction represented by a solid line. Thereafter, the prediction device 1 only needs to execute the processing of S8 and after.

[Summary]

As illustrated in FIG. 8, the prediction device 1 includes: the communication device 16 that acquires the measurement subject data including the measurement data of the shape of the foot of the measurement subject person in the loaded state; the storage 13 that stores the first sample data in the loaded state and the second sample data in an unloaded state, the first sample data and the second sample data being calculated from the measurement data of the foot shapes of the plurality of samples, the samples being identical both in the loaded state and the unloaded state; and the processor 11 that predicts the shape of the foot of the measurement subject person in the unloaded state. As illustrated in FIG. 14, the processor 11 calculates the difference between the measurement subject data and the first sample data (S8), and predicts the shape of the foot of the measurement subject person in the unloaded state based on the difference and the second sample data (S9).

Accordingly, by using the first sample data in the loaded state and the second sample data in the unloaded state, the prediction device 1 can predict the shape of the foot of the measurement subject person in the unloaded state from the measurement data of the shape of the foot of the measurement subject person in the loaded state. Therefore, the user of the prediction device 1 can easily acquire the shape of the foot of the measurement subject person in the unloaded state using the prediction device 1 only by measuring the shape of the foot of the measurement subject person in the loaded state.

As illustrated in FIG. 10, the first sample data is obtained by classifying the measurement data of the foot shapes of the plurality of samples in the loaded state for each of a plurality of foot shape types based on at least one feature amount related to the shape of the foot. As illustrated in FIG. 13, the second sample data is obtained by classifying the measurement data of the foot shapes of the plurality of samples in the unloaded state according to the plurality of foot shape types based on the at least one feature amount. As illustrated in FIG. 14, the processor 11: selects one foot shape type from the plurality of foot shape types based on the measurement subject data (S3); calculates a difference between the measurement subject data and the first sample data that belongs to the one foot shape type (S8); and predicts the shape of the foot of the measurement subject person in the unloaded state based on the difference and the second sample data that belongs to the one foot shape type (S9).

As a result, the prediction device 1 can predict the shape of the foot of the measurement subject person in the unloaded state using the first sample data and the second sample data that match the foot shape type of the foot of the measurement subject person in the loaded state. Therefore, the prediction device 1 can improve accuracy in the prediction of the shape of the foot of the measurement subject person in the unloaded state.

As illustrated in FIG. 10, the first sample data is obtained by averaging the measurement data of the foot shapes of the plurality of samples in the loaded state for each of the plurality of foot shape types. As illustrated in FIG. 13, the second sample data is obtained by averaging the measurement data of the foot shapes of the plurality of samples in the unloaded state for each of the plurality of foot shape types.

As a result, the prediction device 1 can predict the shape of the foot of the measurement subject person in the unloaded state using the averaged first sample data and the averaged second sample data that match the foot shape type of the foot of the measurement subject person in the loaded state. Therefore, since the prediction device 1 does not need to store an enormous amount of first sample data and second sample data, it is possible to suppress an increase in consumed capacity of the storage 13.

As illustrated in FIG. 14, the processor 11: calculates the first sample data after change by changing a length and a width of a foot included in the first sample data that belongs to the one foot shape type in accordance with a length and a width of a foot included in the measurement subject data (S6); calculates the second sample data after change by changing a length and a width of a foot included in the second sample data that belongs to the one foot shape type in accordance with the length and the width of the foot included in the measurement subject data (S7); calculates the difference by comparing a degree of bending of the foot included in the measurement subject data with a degree of bending of a foot included in the first sample data after the change (S8); and predicts the shape of the foot of the measurement subject person in the unloaded state by changing a degree of bending of the foot included in the second sample data after the change based on the difference (S9).

As a result, the prediction device 1 can predict the shape of the foot of the measurement subject person in the unloaded state by changing the length and width of the foot in each of the first sample data and the second sample data in accordance with the length and width of the foot included in the measurement subject data, and then changing the degree of bending of the foot in the second sample data so as to match the degree of bending of the foot included in the measurement subject data. Therefore, the prediction device 1 can further improve accuracy in the prediction of the shape of the foot of the measurement subject person in the unloaded state.

As illustrated in FIGS. 18A to 18C, the processor 11: corrects the first sample data after the change based on a length of an arch (apparent arch) on a side of the foot included in the measurement subject data; and corrects the second sample data after the change based on a length of an arch (apparent arch) on a side of the foot included in the measurement subject data.

Accordingly, since the prediction device 1 corrects the first sample data and the second sample data based on the apparent arch length of the foot included in the measurement subject data, the first sample data and the second sample data can be brought closer to the foot of the measurement subject data. Therefore, the prediction device 1 can further improve accuracy in the prediction of the shape of the foot of the measurement subject person in the unloaded state.

The at least one feature amount includes one of a foot arch height ratio, a heel angle, a ball girth, a degree of bending of a foot, a toe shape, and an age.

As a result, the prediction device 1 can classify the measurement subject data, the first sample data, and the second sample data based on any one of the foot arch height ratio, the heel angle, the ball girth, the degree of bending of the foot, the shape of the toe, and the age. Furthermore, the prediction device 1 can classify the measurement subject data, the first sample data, and the second sample data in more detail by increasing types of feature amounts used for classification.

As illustrated in FIG. 1, the measurement subject data includes measurement data of a shape of a foot measured in a state in which the measurement subject person is in a standing posture. As illustrated in FIG. 10, the first sample data is calculated from measurement data of foot shapes of the plurality of samples measured in a state in which a plurality of sample subjects are in the standing posture.

As a result, the user of the prediction device 1 can easily acquire the shape of the foot of the measurement subject person in the unloaded state using the prediction device 1 only by measuring the foot of the measurement subject person in the standing posture who has visited the store. Therefore, it is not always necessary for an expert with skills to measure the shape of the foot of the measurement subject person, and convenience in the store is improved.

A prediction method by the processor 11 for predicting a shape of a foot of a measurement subject person in an unloaded state, the prediction method includes: acquiring measurement subject data including measurement data of the shape of the foot of the measurement subject person in a loaded state; storing first sample data in the loaded state and second sample data in the unloaded state, the first sample data and the second sample data being calculated from measurement data of foot shapes of a plurality of samples, the samples being identical both in the loaded state and the unloaded state; and predicting the shape of the foot of the measurement subject person in the unloaded state. As illustrated in FIG. 14, the predicting includes: calculating a difference between the measurement subject data and the first sample data (S8); and predicting the shape of the foot of the measurement subject person in the unloaded state based on the difference and the second sample data (S9).

Accordingly, by using the first sample data in the loaded state and the second sample data in the unloaded state, the prediction device 1 can predict the shape of the foot of the measurement subject person in the unloaded state from the measurement data of the shape of the foot of the measurement subject person in the loaded state. Therefore, the user of the prediction device 1 can easily acquire the shape of the foot of the measurement subject person in the unloaded state using the prediction device 1 only by measuring the shape of the foot of the measurement subject person in the loaded state.

As illustrated in FIG. 1, the prediction system 100 includes: the measurement device 2 that measures a shape of a foot of a measurement subject person in a loaded state; and the prediction device 1 that predicts the shape of the foot of the measurement subject person in the unloaded state. As illustrated in FIG. 8, the prediction device 1 includes: the communication device 16 that acquires, from the measurement device 2, the measurement subject data including the measurement data of the shape of the foot of the measurement subject person in the loaded state; the storage 13 that stores the first sample data in the loaded state and the second sample data in an unloaded state, the first sample data and the second sample data being calculated from the measurement data of the foot shapes of the plurality of samples, the samples being identical both in the loaded state and the unloaded state; and the processor 11 that predicts the shape of the foot of the measurement subject person in the unloaded state. As illustrated in FIG. 14, the processor 11 calculates the difference between the measurement subject data and the first sample data (S8), and predicts the shape of the foot of the measurement subject person in the unloaded state based on the difference and the second sample data (S9).

Accordingly, by using the first sample data in the loaded state and the second sample data in the unloaded state, the prediction system 100 can predict the shape of the foot of the measurement subject person in the unloaded state from the measurement data of the shape of the foot of the measurement subject person in the loaded state. Therefore, the user of the prediction system 100 can easily acquire the shape of the foot of the measurement subject person in the unloaded state using the prediction device 1 only by measuring the shape of the foot of the measurement subject person in the loaded state.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A prediction device that predicts a shape of a foot of a measurement subject person in an unloaded state, the prediction device comprising:
   an acquisition unit configured to acquire measurement subject data including measurement data of the shape of the foot of the measurement subject person in a loaded state;
   a storage unit which stores a database of previously measured first sample data in the loaded state and previously measured second sample data in the unloaded state, the previously measured first sample data and the previously measured second sample data being previously calculated from measurement data of foot shapes of a plurality of samples, the samples being identical both in the loaded state and the unloaded state; and
   a prediction unit configured to:
      calculate a difference between the measurement subject data and the previously measured first sample data; and
      predict the shape of the foot of the measurement subject person in the unloaded state based on the difference and the previously measured second sample data.

2. The prediction device according to claim 1, wherein
   the previously measured first sample data is obtained by classifying the measurement data of the foot shapes of the plurality of samples in the loaded state for each of a plurality of foot shape types based on at least one feature amount related to the shape of the foot,
   the previously measured second sample data is obtained by classifying the measurement data of the foot shapes of the plurality of samples in the unloaded state according to the plurality of foot shape types based on the at least one feature amount, and
   the prediction unit is configured to:
      select one foot shape type from the plurality of foot shape types based on the measurement subject data;
      calculate the difference between the measurement subject data and the previously measured first sample data that belongs to the one foot shape type; and
      predict the shape of the foot of the measurement subject person in the unloaded state based on the difference and the previously measured second sample data that belongs to the one foot shape type.

3. The prediction device according to claim 2, wherein
   the previously measured first sample data is obtained by averaging the measurement data of the foot shapes of the plurality of samples in the loaded state for each of the plurality of foot shape types, and
   the previously measured second sample data is obtained by averaging the measurement data of the foot shapes of the plurality of samples in the unloaded state for each of the plurality of foot shape types.

4. The prediction device according to claim 3, wherein
   the prediction unit is configured to:
   calculate the previously measured first sample data after change by changing a length and a width of a foot included in the previously measured first sample data that belongs to the one foot shape type in accordance with a length and a width of a foot included in the measurement subject data;
   calculate the previously measured second sample data after change by changing a length and a width of a foot included in the previously measured second sample data that belongs to the one foot shape type in accordance with the length and the width of the foot included in the measurement subject data;
   calculate the difference by comparing a degree of bending of the foot included in the measurement subject data with a degree of bending of a foot included in the previously measured first sample data after the change; and
   predict the shape of the foot of the measurement subject person in the unloaded state by changing a degree of bending of the foot included in the previously measured second sample data after the change based on the difference.

5. The prediction device according to claim 4, wherein
   the prediction unit is configured to:
   correct the previously measured first sample data after the change based on a length of an arch on a side of the foot included in the measurement subject data; and
   correct the previously measured second sample data after the change based on a length of an arch on a side of the foot included in the measurement subject data.

6. The prediction device according to claim 2, wherein
   the at least one feature amount includes one of a foot arch height ratio, a heel angle, a ball girth, a degree of bending of a foot, a toe shape, and an age of the measurement subject person.

7. The prediction device according to claim 1, wherein
   the measurement subject data includes measurement data of a shape of a foot measured in a state in which the measurement subject person is in a standing posture, and
   the previously measured first sample data is calculated from measurement data of foot shapes of the plurality of samples measured in a state in which a plurality of sample subjects are in the standing posture.

8. A prediction method by a computer for predicting a shape of a foot of a measurement subject person in an unloaded state, the prediction method comprising:
   acquiring measurement subject data including measurement data of the shape of the foot of the measurement subject person in a loaded state;
   storing a database of previously measured first sample data in the loaded state and previously measured second sample data in the unloaded state, the previously measured first sample data and the previously measured second sample data being previously calculated from measurement data of foot shapes of a plurality of samples, the samples being identical both in the loaded state and the unloaded state;
   calculating a difference between the measurement subject data and the previously measured first sample data; and
   predicting the shape of the foot of the measurement subject person in the unloaded state based on the difference and the previously measured second sample data.

9. A prediction system comprising:
a measurement device configured to measure a shape of a foot of a measurement subject person in a loaded state; and
a prediction device configured to predict the shape of the foot of the measurement subject person in an unloaded state,
wherein the prediction device includes:
an acquisition unit configured to acquire measurement subject data from a measurement device, the measurement subject data including measurement data of a shape of a foot of a measurement subject person in a loaded state;
a storage unit configured to store a database of previously measured first sample data in the loaded state and previously measured second sample data in an unloaded state, the previously measured first sample data and the previously measured second sample data being calculated from measurement data of foot shapes of a plurality of samples, the samples being identical both in the loaded state and the unloaded state; and
a prediction unit configured to:
  calculate a difference between the measurement subject data and the previously measured first sample data, and
predict the shape of the foot of the measurement subject person in the unloaded state based on the difference and the previously measured second sample data.

\* \* \* \* \*